Figure 1:
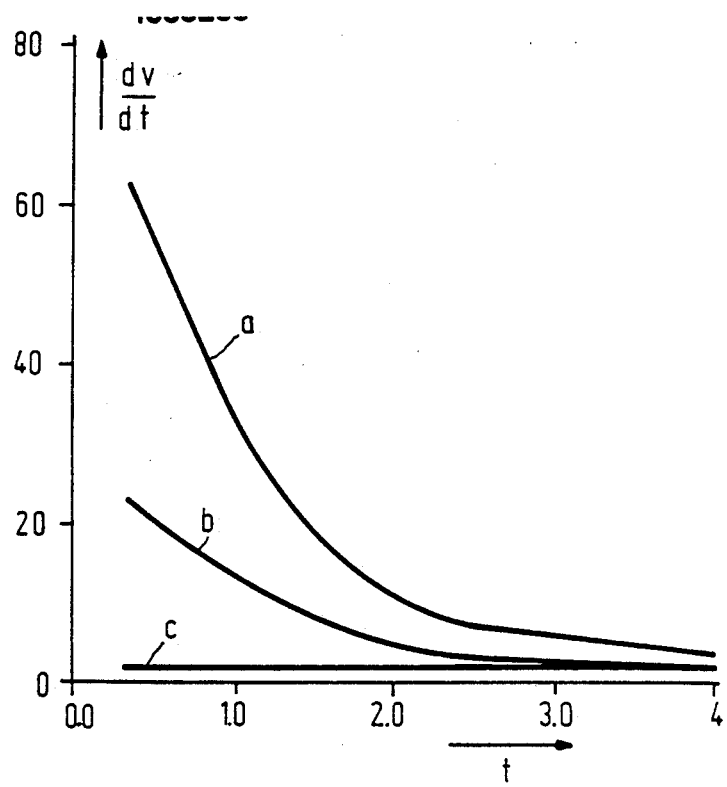

United States Patent [19]

Hillen et al.

[11] Patent Number: 4,998,266
[45] Date of Patent: Mar. 5, 1991

[54] DEVICE FOR PRODUCING X-RAY IMAGES BY MEANS OF A PHOTOCONDUCTOR

[75] Inventors: Walter Hillen; Peter Quadflieg; Ulrich Schiebel, all of Aachen, Fed. Rep. of Germany

[73] Assignee: U.S. Philips Corporation, New York, N.Y.

[21] Appl. No.: 545,672

[22] Filed: Jun. 27, 1990

Related U.S. Application Data

[63] Continuation of Ser. No. 347,597, May 2, 1989, abandoned.

[30] Foreign Application Priority Data

May 6, 1988 [DE] Fed. Rep. of Germany ....... 3815458

[51] Int. Cl.$^5$ .......................................... G03G 13/044
[52] U.S. Cl. .......................................... 378/31; 378/28
[58] Field of Search ...................................... 378/28–33; 250/324, 326; 361/229, 230; 355/3 CH

[56] References Cited

U.S. PATENT DOCUMENTS

| | | | |
|---|---|---|---|
| 2,777,957 | 1/1957 | Walkup. | |
| 3,688,107 | 8/1972 | Schneider et al. | 250/324 |
| 3,772,010 | 11/1973 | Weiss | 378/31 |
| 3,883,740 | 5/1975 | Prondian | 378/30 |
| 3,906,228 | 9/1975 | Lange | 378/28 |
| 4,064,439 | 12/1977 | Yang | 378/31 |
| 4,156,140 | 5/1979 | Lafferty et al. | 378/31 |
| 4,218,619 | 8/1980 | Yang et al. | 378/32 |
| 4,233,541 | 11/1980 | Harada et al. | 250/324 |
| 4,379,969 | 4/1983 | Cobb et al. | 250/324 |
| 4,389,610 | 6/1983 | Schiebel et al. . | |
| 4,535,468 | 8/1985 | Kempter | 378/31 |
| 4,868,907 | 9/1989 | Folkins | 250/324 |

FOREIGN PATENT DOCUMENTS 1399732 7/1975 United Kingdom .
1561945 3/1980 United Kingdom .

Primary Examiner—Craig E. Church
Attorney, Agent, or Firm—William Squire

[57] ABSTRACT

The invention relates to a device for producing X-ray images by means of a photoconductor which converts X-rays into a charge pattern, which photoconductor is charged prior to the X-ray exposure, its surface being scanned after the exposure in order to detect the charge pattern. Artefacts are liable to occur in an X-ray image when the exposure directly follows an X-ray exposure during which the photoconductor has received, at least in given areas, a high dose. These artegacts are avoided in accordance with the invention in that there is provided a recharging device which limits the decrease of the charge density on the surface of the photoconductor during the X-ray exposure to a predetermined value.

16 Claims, 2 Drawing Sheets

DEVICE FOR PRODUCING X-RAY IMAGES BY MEANS OF A PHOTOCONDUCTOR

This is a continuation of application Ser. No. 347,597, filed May 2, 1989, abandoned.

The invention relates to a device for producing X-ray images by means of a photoconductor which converts X-rays into a charge pattern and which is charged prior to the X-ray exposure, its surface being scanned after exposure in order to detect the charge pattern. A similar device is known essentially from DE-OS 29 48 660corresponding to U.S. Pat. No. 4,389,610.

An ideal photoconductor is an insulator when it is not exposed. It is only during exposure or irradiation by X-rays that it becomes conductive, its conductivity being higher as the radiation intensity is higher. Thus, at the irradiated areas the charge density produced during prior charging is reduced as a function of the dose whereto the relevant area is exposed. The two-dimensional charge pattern thus produced on the surface of the photoconductor, corresponding essentially to the spatial distribution of the X-ray dose ("latent image" or "charge image") is converted into electric signals by the scanning device. These signals are amplified, filtered, digitized and stored. They are then available for digital image processing.

During the formation of X-ray images by means of such a device, artefacts are liable to occur in the X-ray image thus formed when another X-ray image has been formed briefly therebefore. It is the object of the invention to construct a device of the kind set forth so that the occurrence of said artefacts is mitigated. This object is achieved in accordance with the invention in that there is provided a recharging device which limits the decrease of the charge density on the surface of the photoconductor during the X-ray exposure to a predetermined value.

The invention is based on the recognition of the fact that the described artefacts are caused by the fact that, after the recharging of the photoconductor subsequent to an X-ray exposure, the areas which were particularly strongly exposed to X-rays during the preceding exposure are particularly quickly discharged, that is to say also in the dark, and that this effect is due to the fact that the photoconductor was particularly strongly discharged at the relevant areas during the X-ray exposure. Because the discharging during the exposure is limited to a predetermined value, such strong discharging is prevented, so that the photoconductor cannot be particularly quickly discharged at the relevant areas after recharging.

The recharging device in principle consists of a charge carrier source whose potential is chosen so that the surface of the photoconductor is charged when the charge density drops below a presettable value. A preferred embodiment of such a recharging device is characterized in that it comprises a corona discharge device, between said corona discharge device and the photoconductor there being arranged a grid which covers the area of the photoconductor which can be exposed during an X-ray exposure and which limits the potential of the photoconductor surface to a value which corresponds approximately to the grid potential.

In a further embodiment in accordance with the invention, the corona discharge device serves for charging the photoconductor prior to an X-ray exposure, it being possible to reduce the voltage between the grid and the conductive substrate supporting the photoconductor to a lower value after such charging.

A corona discharge device comprises one or more parallel wires which are connected to a high voltage in the operating condition, thus causing a corona discharge. In order to prevent these wires from being imaged in the X-ray image, in a further embodiment in accordance with the invention there is provided a drive for producing a relative motion between the grid and the surface of the photoconductor.

Figure 2:
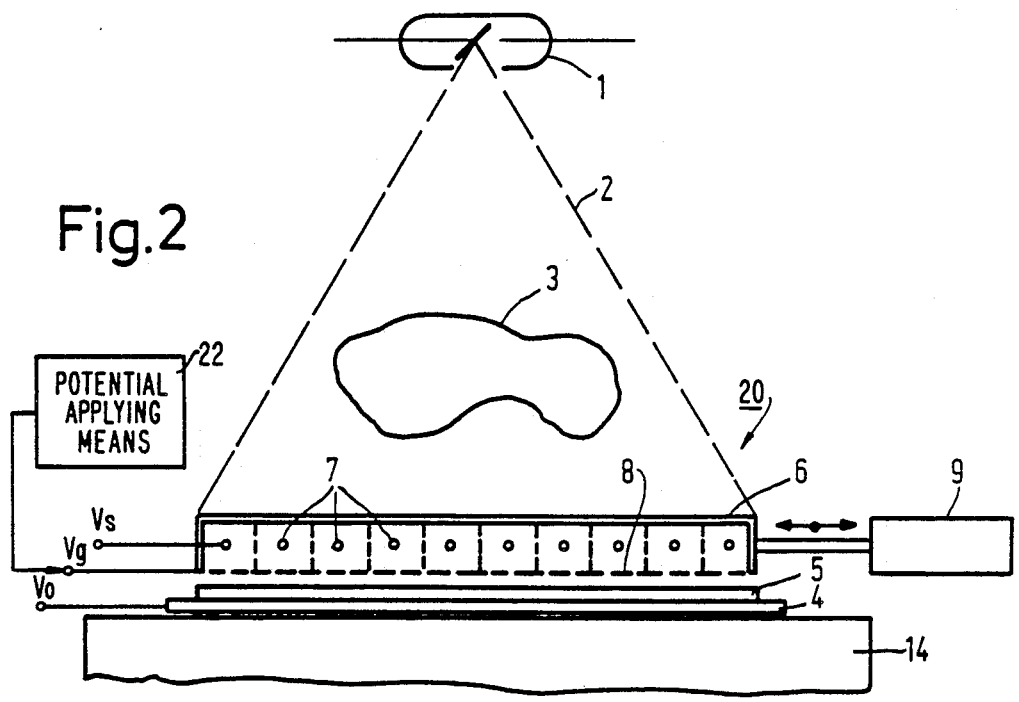
Figure 3:
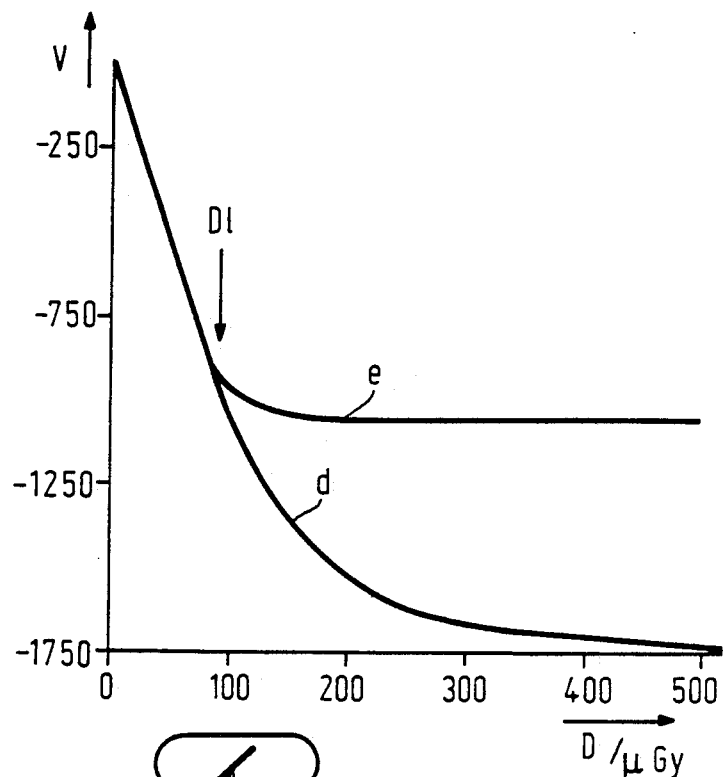
Figure 4:
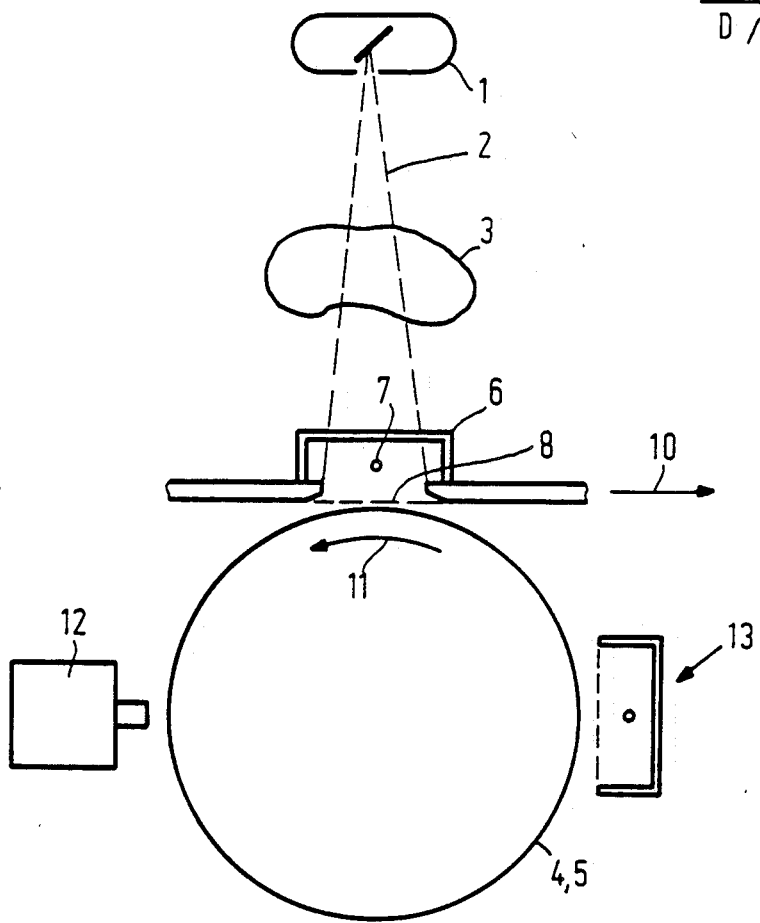

The invention will be described in detail hereinafter with reference to the drawing. Therein:

FIG. 1 shows the rate of change as a function of time of the potential on the surface of a photoconductor for different exposures, FIG. 2 shows a device in accordance with the invention, FIG. 3 shows the variation of the surface potential with and without the steps proposed in accordance with the invention, and FIG. 4 shows a further embodiment in accordance with the invention.

When the surface of a photoconductor, for example consisting of amorphous selenium, is exposed to a comparatively high radiation dose ($>100$ $\mu$Gy), immediately after the subsequent charging the dark discharge rate, i.e. the variation of the surface potential per unit of time for a non-exposed photoconductor is initially strongly increased. In the course of a few minutes, it is reduced to its normal value again. The curve a in FIG. 1 represents a typical variation in time of the dark discharge rate (expressed in V/min) subsequent to an X-ray exposure using a dose of 1 mGy; the time is shown in minutes. For comparison the curve c represents the dark discharge rate of the same photoconductor without prior exposure.

In medical X-ray diagnostics a dose in the order of magnitude of 1 mGy will often be incident on at parts of the photoconductor, because the irradiated objects partly absorb a very large part of the radiation. At the actual image area only doses of the order of magnitude of from 1 to 10 $\mu$Gy are then incident on the photoconductor, but given areas of the photoconductor will inevitably be exposed to the unattenuated direct radiation.

For an exposure frequency of 1/min or more, in accordance with FIG. 1 the situation arises in which the dark discharge rate varies strongly in time at the areas of the photoconductor which have been strongly exposed under the influence of direct radiation during the preceding exposure. Consequently, at the instant at which the charge pattern on the surface of the photoconductor is scanned with an influence probe device the charge pattern no longer exactly represents the X-ray image, thus causing the described artefacts. This also makes the correction of the dark discharge effect by subtraction of a dark discharge image, as described in German Patent Application P 35 29 108, substantially more difficult.

The described increased dark discharge rate is substantially reduced in accordance with the invention.

FIG. 2 shows a device in accordance with the invention. The reference numeral 1 denotes an X-ray source which produces an X-ray beam 2 which irradiates a patient 3 and which is converted into a charge pattern by a photoconductor device. The photoconductor device consists of a layer 5 of selenium doped with 0.5% arsenide, which has a layer thickness of 0.5 mm and is provided on an aluminium electrode 4. The aluminium electrode is provided on a suitable insulating substrate 14. At a small distance from the selenium layer 5 there is provided a grid-controlled corona discharge device. This device 20 comprises a corona discharge assembly 21 and a voltage controlled grid 8. Assembly 21 includes a housing 6 whose material and wall thickness are chosen so that the X-rays are not significantly attenuated thereby. It may consist of a thin aluminium sheet or a plastics sheet metallized with a thin layer on one side. The conductive housing wall is grounded. The dimensions of the housing correspond to the dimensions of the photoconductor layer.

In the housing there are provided wires 7 which extend parallel to one another and to the surface of the photoconductor 5 and which are electrically conductively interconnected. The wires 7 receive a voltage $V_s$ for creating a corona discharge. On its side facing the photoconductor layer 5, the housing 6 is closed by an electrically controllable grid 8. The grid is situated at a small distance from the photoconductor (typically from 0.2 to 2.0 mm) and has a small mesh size (typically from 0.1 to 0.5 mm).

Prior to the X-ray exposure, the surface of the photoconductor layer 5 is charged by the device 20. To this end a voltage Vo of, for example—1,750 V' (with respect to the housing 6) is applied to the aluminium electrode 4. A positive high $V_s$ voltage Vs is applied to the wires 7 to create the corona discharge. A voltage $V_g$ is applied to the grid 8 by potential applying means 22. The value of the positive voltage is chosen so that the surface of the photoconductor layer 5 is charged to the potential $V_g$ of the grid 8 within a period of from 10 to 100 ms. At this time grid potential $V_{g1}$ of grid 8 either corresponds to ground potential (0 V) or is slightly negative via potential applying means 22, so that all charge carriers generated around the wires 7 by the corona discharge are accelerated towards the grid 8. When the potential on the surface of the photoconductor layer 5 reaches the grid potential $V_{g1}$, the charge carriers emitted by the wires 7 are captured by the grid and no longer reach the photoconductor layer 5. Thus, the desired surface potential $V_{g1}$ of layer 5 is substantially accurately created on the surface thereof, so that the fluctuations of the layer 5 surface potential which are imposed by the construction of the grid-controlled corona discharge device 20 are less than 0.1 V.

If the corona discharge were deactivated after charging or at the beginning of the X-ray exposure, the photoconductor layer 5 would be discharged during the subsequent X-ray exposure at a rate which is essentially proportional to the X-ray dose power. Discharging ceases only when the charge on the surface of the photoconductor has decayed, unless the X-ray tube 1 was previously switched off to a value corresponding to $V_g$. The variation of the layer 5 surface potential as a function of the X-ray dose (measured in μgy) occurring during the X-ray exposure would vary typically as represented by the curve d in FIG. 3. As shown, curve d approaches the $V_o$—1750 volt potential of electrode 4.

In accordance with the invention, however, the corona discharge device 20 is not deactivated during the X-ray exposure; instead, it continues to operate and only the difference Vg—Vo between the grid 8 potential $V_{g2}$ and the substrate potential is reduced for by potential applying means 22. For example, by means 22 a negative potential $V_{g2}$ of —900 V is now applied to the control grid 8. The discharging of the potoconductor is thus terminated as soon as its surface potential reaches the value 900 V of the grid 8 potential at any area of layer 5. This is because the control grid 8 then becomes transparent for positive charge carriers emitted by assembly 21 so that these charge carriers pass from wires 7 through grid 8 and reach the corresponding areas of the surface of the photoconductor, layer 5 which otherwise would discharge t a level toward the potential of $V_o$. This action limits the discharge current induced by the irradiation by recharging layer 5 to $V_{g2}$. The surface potential then varies as a function of the radiation dose as represented by the curve e in FIG. 3; this curve is identical to the curve d up to a limit dose D1 of approximately 100 μGy, but is substantially independent from the radiation dose thereafter. Note that the decrease of the potential of layer 5 is limited to —900 V of $V_{g2}$ applied to grid 8.

The curve b in FIG. 1 illustrates the variation in time of the dark discharge rate for a photoconductor which is recharged in accordance with the curve e of FIG. 3 when the charge density or the potential on the surface drops below a limit value, e.g., —900 V, $V_{g2}$ so that a predetermined potential or a predetermined charge density arises at the relevant areas. It appears that this limitation of the charge density or the potential on the surface of layer 5 substantially reduces the dark discharge effect in comparison with a dark discharge without recharging for the preceding exposure (curve a). In other words, the discharge potential value of layer 5 is not determined by $V_o$, but by $V_{g2}$ which is at a higher voltage than $V_o$. Whenever the potential of an area of the surface of layer 5 tends to go below $V_{g2}$, —900 V, the system then automatically recharges the layer 5 to —900 V at that region.

The limitation of the charge density or the surface potential, however, also limits the dynamic range of the photoconductor and the image information contained in the recharged areas is lost. In the example illustrated by the curve e in FIG. 3, the limit dose amounts to approximately 100 μGy; it can be increased, if necessary, to approximately 200 μGy by increasing the electrode voltage Vo or by reducing Vg. For medical diagnostic applications the mean doses are between 1 and 10 μGy. Thus, generally speaking adequate room for varying this exposure in the upwards direction remains.

For the exposure technique customarily used in projection radiography the photoconductor is flat and has maximum dimensions of 450×450 mm²; all areas of the photoconductor are simultaneously exposed. For performing the recharging method, therefore, a corona device is required which covers the entire sector area. The wires 7 and the grid 8 are liable to be imaged during an X-ray exposure, because they absorb X-rays. Such imaging, however, can be prevented by reciprocating the housing 6, together with the components contained therein, at a suitable frequency and amplitude by means of a drive 9 during the X-ray exposure (as in the case of a scatter grid), so that the structures of these parts in the image are blurred.

The construction of the corona device 20 is substantially simpler when the method is used in an apparatus for slit radiography, for example as known from DE-OS 35 34 768. FIG. 4 shows such an apparatus which will be described hereinafter. Only a comparatively narrow radiation beam 2 is formed from the X-rays emitted by the X-ray source 1, which beam irradiates only a part of the object to be examined and exposes only a part of the photoconductor 4, 5 which is situated on the surface of a drum which rotates during the X-ray exposure. Imaging is realized in that the surface of the photoconductor 4, 5 as well as the object 3 on the one side and the radiation beam 2 on the other side are moved relative to one another, as denoted by the arrows 10 and 11, so that the X-ray image of the complete object 3 appears on the cylindrical surface of the photoconductor 4, 5; this image is scanned by means of a diagrammatically shown influence probing device 12 for digital processing.

In that case the corona discharge device need merely cover the strip of the photoconductor surface which is each time exposed during the X-ray exposure. Therefore, the dimensions of the device 6 . . . 8 can be substantially reduced. The relative motion between the photoconductor and the exposure slit prevents the structures of the corona dischage device from being imaged in the X-ray image. An additional drive (like the device 9 in FIG. 2), therefore, can be dispensed with. The corona discharge device 6, 7, 8 required for recharging can also serve, like the device shown in FIG. 2, for charging the photoconductor 4, 5 prior to the X-ray exposure. In that case the corona discharge device 13 for charging which is situated outside the beam path can be dispensed with.

What is claimed is:

1. X-ray imaging apparatus comprising:
   a source of X-ray radiation;
   a photoconductor responsive to said radiation incident thereon;
   means for charging the photoconductor to a first potential value relative to a second potential value, said photoconductor for converting said incident X-ray radiation into a charge pattern, said photoconductor discharging in accordance with the intensity of the incident radiation, at least a portion of said photoconductor discharging to a charge density corresponding to said second potential value in response to said incident radiation unless otherwise precluded;
   means for exposing said photoconductor to said radiation; and
   recharge means for simultaneously recharging the photoconductor during said exposure with a given charge to a third potential value intermediate said first and second potential values during exposure to said radiation to limit the decrease in said charge density of said photoconductor to a value corresponding to said third potential.

2. The apparatus as claimed in claim 5, characterized in that the recharge means comprises a corona discharge device including a grid, said grid being placed at said first and third potentials and located between the discharge device and photoconductor adjacent to a surface of the photoconductor, said grid being dimensioned to cover the area of the photoconductor exposed during said x-ray radiation exposure, said third potential of said grid limiting the potential of the photoconductor surface to a value which corresponds approximately to the grid third potential.

3. The apparatus as claimed in claim 2, characterized in that the means for charging includes means for initially charging the photoconductor with a given first potential value applied to said grid prior to said photoconductor receiving said incident radiation and said recharge means includes means for reducing the given first potential value to the third potential value to charge the photoconductor with a potential of a lower value after such initial charging.

4. A device as claimed in claim 2, characterized in that there is provided a drive for producing a relative motion between the corona discharge device and the photoconductor.

5. The apparatus of claim 1 wherein said recharge means includes corona discharge means and grid means between said source and said photoconductor, said apparatus further including means for displacing the photoconductor, discharge means and grid means relative to said source.

6. An X-ray imaging apparatus comprising:
   a source of X-ray radiation;
   a photoconductor responsive to said radiation incident thereon for producing an image;
   means for exposing the photo conductor to said radiation;
   means for charging the photoconductor with a charge of a given level prior to exposing the photoconductor to said radiation; and
   means for charging the photoconductor with a charge of a different level than said given level simultaneously with the exposing of the photoconductor to said radiation to limit the discharge caused by said incident radiation to said different level.

7. The apparatus of claim 6 wherein each said means for charging comprises corona discharge means for charging the photoconductor in response to an applied voltage and means for setting the voltage applied to said discharge means to different respective values so as to charge said photoconductor with said given and different charge levels.

8. The apparatus of claim 7 wherein said means for exposing included aperture means for exposing a first portion of said photoconductor to said radiation and photoconductor displacement means for displacing the photoconductor to expose a second portion of the photoconductor to said radiation subsequent to the exposure of the first portion.

9. An X-ray imaging apparatus comprising:
   an X-ray source for emission of X-ray radiation; and
   a detection device for converting the X-ray radiation into a charge density pattern;
   said detection device comprising:
      a photoconductor at a first potential Vo;
      means for positioning the photoconductor for exposure to said radiation;
      charging means at a second potential Vg1 different than the first potential Vo for charging the photoconductor with a charge density of a value corresponding to said second potential, the charge density being reduced over an area of said photoconductor exposed to said radiation in accordance with the radiation intensity and first potential value; and
      recharge means at a third potential Vg2 having a value intermediate that of the first and second potentials during said exposure for recharging to said third potential those portions of said area which otherwise would discharge to said first potential.

10. The apparatus of claim 9 wherein said means for positioning includes drive means for producing relative motion between said detection device and said source during said exposure.

11. The apparatus of claim 9 wherein said charging means comprises a corona discharge device at a fourth potential, a grid located between said device and said photoconductor and means for applying said second potential to said grid prior to said exposure.

12. The apparatus of claim 11 wherein the recharging means comprises means for applying said third potential to said grid during said exposure.

13. The apparatus of claim 11 wherein the discharge device and the grid cover substantially all of the area of the photoconductor exposed to said radiation.

14. A detection device for converting X-ray radiation into a charge density pattern, said device comprising:
   a photoconductor;
   means for positioning the photoconductor for exposure to said radiation;
   charging means for charging the photoconductor with a predetermined charge density to a first level, the charge density being reduced over an area of said photoconductor that is exposed to said radiation; and
   recharge means for recharging at least a portion of said area during exposure to said radiation when the charge density of said at least a portion of said area reaches a predetermined level different than the first level.

15. The device of claim 14 wherein said means for positioning includes drive means for displacing said detection device relative to said radiation during said exposure.

16. The device of claim 14 wherein said charging means comprises a corona discharge device and a voltage control grid adjacent to the photoconductor at a first potential and said recharge means comprises placing said grid at a second potential different than the first potential for limiting the potential at the surface of the photoconductor to a value corresponding to said second potential.

* * * * *